United States Patent [19]

Hauser

[11] Patent Number: 4,946,984
[45] Date of Patent: Aug. 7, 1990

[54] ALKOXYLATION USING A CALCIUM SULFATE CATALYST

[75] Inventor: Charles F. Hauser, Charleston, W. Va.

[73] Assignee: Union Carbide Chemicals and Plastics Company Inc., Danbury, Conn.

[21] Appl. No.: 251,430

[22] Filed: Sep. 30, 1988

[51] Int. Cl.$^5$ .............................................. C07C 41/03
[52] U.S. Cl. ................... 568/618; 568/606; 568/607; 568/608; 568/609; 568/610; 568/619; 568/620
[58] Field of Search ............... 568/606, 607, 608, 609, 568/610, 618, 619, 620

[56] References Cited

U.S. PATENT DOCUMENTS

| 2,934,505 | 4/1960 | Gurgiolo | 260/2 |
| 3,328,306 | 6/1967 | Ellis | 252/90 |
| 3,432,445 | 3/1969 | Oagan et al. | 260/2 |
| 3,607,785 | 9/1971 | Oagan et al. | 252/431 C |
| 3,682,849 | 8/1972 | Smith et al. | 260/615 B |
| 4,098,818 | 7/1978 | Krummel et al. | 260/535 R |
| 4,112,231 | 9/1978 | Weibull et al. | 544/174 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,281,087 | 7/1981 | Heuschen et al. | 525/361 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,326,047 | 4/1982 | Yates | 525/507 |
| 4,359,589 | 11/1982 | Brownscombe | 568/618 |
| 4,360,698 | 11/1982 | Sedon | 568/618 |
| 4,375,564 | 3/1983 | Edwards | 568/618 |
| 4,396,779 | 8/1983 | Edwards | 568/618 |
| 4,396,780 | 8/1983 | Shtykh et al. | 568/620 |
| 4,453,022 | 6/1984 | McCain et al. | 568/618 |
| 4,453,023 | 6/1984 | McCain et al. | 568/618 |
| 4,465,877 | 8/1984 | Edwards | 568/618 |
| 4,472,560 | 9/1984 | Kuyper et al. | 526/120 |
| 4,474,678 | 10/1984 | Lutz et al. | 252/174.21 |
| 4,477,589 | 10/1984 | van der Hulst et al. | 502/169 |
| 4,490,561 | 12/1984 | Yang et al. | 568/615 |
| 4,568,774 | 2/1986 | Yang | 568/616 |
| 4,654,417 | 3/1987 | Inoue et al. | 528/416 |
| 4,659,778 | 4/1987 | Williams | 525/107 |
| 4,665,236 | 5/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |
| 4,754,075 | 6/1988 | Knopf et al. | 568/618 |
| 4,775,653 | 10/1988 | Leach et al. | 502/170 |

FOREIGN PATENT DOCUMENTS

| 0026544 | 4/1981 | European Pat. Off. . |
| 0026546 | 4/1981 | European Pat. Off. . |
| 0026547 | 4/1981 | European Pat. Off. . |
| 0033359 | 6/1981 | European Pat. Off. . |
| 0082569 | 6/1983 | European Pat. Off. . |
| 0085167 | 6/1983 | European Pat. Off. . |
| 0095562 | 12/1983 | European Pat. Off. . |
| 0104309 | 4/1984 | European Pat. Off. . |
| 0180266 | 5/1986 | European Pat. Off. . |
| 0180267 | 5/1986 | European Pat. Off. . |
| 0212820 | 3/1987 | European Pat. Off. . |
| 1399966 | 7/1975 | United Kingdom . |
| 1462133 | 1/1977 | United Kingdom . |
| 1462134 | 1/1977 | United Kingdom . |

OTHER PUBLICATIONS

Kochurovskaya, G. G. et al., Kriobiol. Kriomed., 3, 1977, pp. 76–79.
Turova, N. Y. et al., Chemical Reviews—Uspekhi Khimii, Mar. 1965, pp. 161–185.
U.S. patent application Ser. No. 186,937, filed Aug. 27, 1988 (D-12555-1).
U.S. patent application Ser. No. 186,938, filed Apr. 27, 1988 (D-12337).
Schick, M. J., Nonionic Surfactants, vol. 1, Marcel Dekker, Inc., New York, N.Y. (1967) pp. 28–41.
U.S. patent application Ser. No. 454,560, filed Dec. 30, 1982 (D-13322).
U.S. patent application Ser. No. 102,939, filed Sep. 30, 1987, (D-15778).

Primary Examiner—Howard T. Mars
Attorney, Agent, or Firm—Gerald L. Coon

[57] ABSTRACT

This invention relates to the use of calcium sulfate as a catalyst in the preparation of alkoxylation products, i.e., condensation reaction products of alkylene oxides and organic compounds having at least one active hydrogen, that have beneficial, narrow molecular weight ranges.

26 Claims, No Drawings

ALKOXYLATION USING A CALCIUM SULFATE CATALYST

RELATED APPLICATIONS

The following are related, commonly assigned applications, filed on an even date herewith:
U.S. patent application Ser. No. 251,433; U.S. patent application Ser. No. 251,434; U.S. patent application Ser. No. 251,432; U.S. patent application Ser. No. 251,436; and U.S. patent application Ser. No. 251,431.

BRIEF SUMMARY OF THE INVENTION

1. Technical Field

This invention relates to the use of calcium sulfate as a catalyst in the preparation of alkoxylation products, i.e., condensation reaction products of alkylene oxides and organic compounds having at least one active hydrogen, that have beneficial, narrow molecular weight ranges.

2. Background of the Invention

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a greater portion of water is usually required otherwise gelling may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation Product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
| --- | --- | --- |
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % |  |  |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published Dec. 12, 1983, exemplifies the ability to obtain high selectivity to low ethoxylate species when low ratios of ethylene oxide reactant to alcohol are employed as well as the tendency to rapidly lose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
| --- | --- | --- |
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Recently, Yang and coworkers were granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093.

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European patent publication Nos. 0026544, 0026547, and 0026546, all herein incorporated by reference. See also U.S. Ser. No. 454,560, filed Dec. 30, 1982 (barium-containing catalyst). These workers have also disclosed the use of strong acids to partially neutralize and thereby promote the catalytic action of certain alkaline earth metal derivatives. See U.S. Pat. Nos. 4,453,022 and 4,453,023 (barium-containing catalyst), both herein incorporated by reference.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

Copending U.S. patent application Ser. No. 621,991, filed June 22, 1984, herein incorporated by reference, relates to processes for preparing alkoxylation mixtures having relatively narrow alkoxylation product distributions using modified, calcium containing catalysts. Processes are also disclosed for making alkoxylation catalysts using calcium oxide and/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

Copending U.S. patent application Ser. No. 102,939 filed Sept. 30, 1987, incorporated herein by reference, relates to heterogeneous (organic polymer-supported) calcium-containing catalysts and the use thereof in the preparation of alkoxylation products, i.e., condensation reaction products of alkylene oxides and organic compounds having at least one active hydrogen. Processes are disclosed for preparing heterogeneous (organic polymer-supported) calcium-containing catalysts for alkoxylation using calcium oxide or calcium hydroxide as sources for the catalytically-active calcium. Also, alkoxylation products are disclosed that have beneficial, narrow molecular weight ranges and are essentially neutral in pH and free from catalyst residues.

Furukawa, Junji and Saegusa, Takeo, Polymerization of Aldehydes and Oxides, Interscience Publishers (1963), page 170, discloses the catalytic activity of calcium sulfate in polymerization of ethylene oxide. U.S. Pat. No. 2,917,470 discloses a process for producing polyolefin oxides using metallic sulfate catalysts. However, as described in U.S. Pat. No. 4,665,236 at column 8, lines 55–58, it is not predictable that catalysts recognized for their activity in promoting polymerization of alkylene oxides would be suitable for use as alkoxylation catalysts.

DISCLOSURE OF THE INVENTION

This invention relates to a process for Preparing alkoxylation product mixtures having relatively narrow alkoxylation product distributions using calcium sulfate as a catalyst.

The alkoxylation process of this invention involves the condensation reaction of an alkylene oxide and at least one organic compound having at least one active hydrogen in the presence of a catalytically effective amount of calcium sulfate. The calcium sulfate catalyst is sufficient to narrow the distribution of the alkoxylation product mixture and provide at least one alkoxylation specie in an amount of at least about 20 weight percent of the mixture.

By the process of this invention, alkoxylation product mixtures are provided which have a narrow, but balanced distribution of alkoxylation species. These product mixtures are relatively free from large amounts of substantially higher alkoxylation moieties, i.e, those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species.

The alkoxylation product mixtures prepared by the processes of this invention are characterized as the condensation reaction products of alkylene oxides and organic compounds having at least one active hydrogen in which the mole ratio of reacted alkylene oxide per active hydrogen is at least about 4, say, about 4 to 16 or 24, preferably about 5 to 12. The product mixtures have at least one alkoxylation moiety which constitutes at least about 20, say, about 20 to 30 or 40, and most often about 20 to 30, weight percent of the composition. The alkoxylation mixtures of this invention also have a relatively symmetrical distribution. Hence, the portion of the product mixture having three or more oxyalkylene unit groups (per active hydrogen site of the organic compound) than the peak alkoxylation specie is relatively minor, e.g., often less than about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation specie is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie are present in a weight ratio to the most prevalent alkoxylation specie of about 0.6:1 to 1:1.

The preferred alkoxylation product mixtures prepared by the process of this invention correspond to the formula $$P_n = A \times e^{-(\bar{n}-n)^2/(2.6+0.4n)}$$

wherein n is the number of oxyalkylene groups per reactive hydrogen site for an alkoxylation specie (must equal at least one) of the composition, $\bar{n}$ is the weight average oxyalkylene number, A is the weight percent of the most prevalent alkoxylation specie in the mixture and $P_n$ is, within plus or minus two percentage points, the weight percent of the alkoxylation specie having n oxyalkylene groups (per active hydrogen site) in the mixture. This distribution relationship generally applies where n is between the amount of $\bar{n}$ minus 4 to the amount of $\bar{n}$ plus 4.

For purposes herein, the average peak alkoxylation specie is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture (including unreacted alcohol), i.e., $\bar{n}$ equals the sum of $(n)(P_n)$ for all the species present divided by 100.

Preferred alkoxylation product mixtures prepared by the process of this invention include poly(oxyethylene)glycols, i.e., CARBOWAX®, and fatty alcohol ethoxylates, i.e., TERGITOL®. CARBOWAX® is the registered trademark of Union Carbide Corporation for a series of poly(oxyethylene)glycols. Ethylene glycol can be used to make the CARBOWAX® poly(oxyethylene)glycols or the CARBOWAX® poly(oxyethylene)glycols can be used to make higher molecular weight CARBOWAX® poly(oxyethylene)glycols. For example, CARBOWAX® poly(oxyethylene)glycol 200 can be used to make CARBOWAX® poly(oxyethylene)glycol 400. Specifically, the CARBOWAX® poly(oxyethylene) glycols are liquid and solid polymers of the general formula $H(OCH_2CH_2)_wOH$, where w is greater than or equal to 4. In general, each CARBOWAX® poly(oxyethylene)glycol is followed by a number which corresponds to its average molecular weight. Examples of useful CARBOWAX® poly(oxyethylene)glycols are: CARBOWAX® Poly(oxyethylene)glycol 200, which has an average w value of 4 and a molecular weight range of 190 to 210; CARBOWAX® poly(oxyethylene)glycol 400, which has an average w value between 8.2 and 9.1 and a molecular weight range of 380 to 420; and CARBOWAX® poly(oxyethylene)glycol 600, which has an average w value between 12.5 and 13.9 and a molecular weight range of 570 to 630.

TERGITOL® is the registered trademark of Union Carbide Corporation for a series of ethoxylated nonylphenols, primary and secondary alcohols, i.e., nonionic surfactants, and the sodium salts of the acid sulfate of secondary alcohols of 10 to 20 carbon atoms, i.e., anionic surfactants. Examples of the TERGITOL® nonionic surfactants include TERGITOL® S Nonionics which have the general formula $CH_3(CH_2)_xCH(CH_3)-O-(CH_2CH_2O)_yH$ wherein x is a value of 9–11 and y is a value of about greater than 1. Examples of the TERGITOL® anionic surfactants include TERGITOL® Anionic 08, which is $C_4H_9CH(C_2H_5)CH_2SO_4-Na$; TERGITOL® Anionic 4, which is $C_4H_9CH(C_2H_5)C_2H_4CH-(SO_4-Na)CH_2CH(CH_3)_2$; and TERGITOL® Anionic 7, which is $C_4H_9CH(C_2H_5)C_2H_4CH(SO_4-Na)C_2H_4CH(C_2H_5)_2$.

DETAILED DESCRIPTION

The alkoxylation is conducted using a catalytically-effective amount of calcium sulfate catalyst, e.g., about 0.001 to 10, often about 0.5 to 5, weight percent based on the weight of the starter component. The starter component is on organic compound having at least one active hydrogen with which the alkylene oxide reacts. The heterogeneous catalyst substantially retains its activity during the alkoxylation, regardless of the amount of alkylene oxide employed. Thus, the amount of catalyst can be based on the amount of starter provided to the alkoxylation zone and not the degree of alkoxylation to be effected.

Normally, the catalyst and the starter component are admixed and then the alkylene oxide is added at the reaction temperature until the desired amount of alkylene oxide has been added, then the product is acidified and can be finished, if desired, in any procedure including stripping unreacted starter material from the product mixture, filtration, or further reaction.

The temperature of the alkoxylation is sufficient to provide a suitable rate of reaction and without degradation of the reactants or reaction products. Often, the temperatures range from between about 50° C. and 270° C., e.g. from about 100° C. to 200° C. The pressure may also vary widely, but when low-boiling alkylene oxides such as ethylene oxide and propylene oxide are employed, a pressurized reactor is preferably used.

The alkoxylation reaction medium is preferably agitated to ensure a good dispersal of the reactants and catalyst throughout the reaction medium. Also, the alkylene oxide is usually added at a rate approximating that which it can be reacted.

The use of acids may assist in reducing and/or eliminating undesired color in the alkoxylation products. Acids that may tend to form catalyst-containing gel structures or solids that clog filtering apparatus should be avoided. Conveniently, sulfuric acid, phosphoric acid, propionic acid, benzoic acid and the like are used.

It is a particularly desirable feature of this invention that the catalyst can be used to provide alkoxylate surfactants having a uniquely narrow molecular weight distribution, low pour point, and low level of unreacted starter component. In this usage, the catalyst is contacted with the starter component, e.g., alcohol, under conditions at which reaction will occur, to perform an alcohol-exchange (which can also be referred to as an alkoxide exchange) reaction. A portion of the starter alcohol thus is present as an alcoholate of calcium, which alcoholate is itself an active species for the alkoxylation reaction. This reaction mixture is then reacted with one or more alkylene oxides, e.g., alkylene oxides such as ethylene oxide, according to known procedures to produce the desired surfactant.

The catalytic alkoxylation reactions of this invention can be effected, for example, by conventional methods such as (1) batch processes; (2) continuous fixed-bed processes; and (3) continuous fluidized reactor processes. In a batch reactor, the catalyst is kept suspended in the reactant by shaking or stirring. In a fluidized reactor, the catalyst is at a particular original level. As the velocity of the reactant stream is increased, the catalyst bed expands upward to a second level, and at a critical velocity it enters into violent turbulence. The fluidized reactor is particularly useful for removing or supplying the heat necessary to maintain a fixed catalyst temperature. The fluidized reactor can usually be employed only on a rather large scale since good fluidization requires a reactor larger than about 1.5 inches in diameter.

The process of this invention broadly involves the use of calcium sulfate catalysts for the alkoxylation of active-hydrogen compounds, preferably hydroxyl-containing compounds, such as, primary or secondary alcohols, diols or triols. Mixtures of active-hydrogen compounds can be used.

Alkoxylation product mixtures prepared by the process of this invention comprise alkoxylation species that can be represented by the formula $$R_{10}[(CHR_{11}-CHR_{12}O)_rH]_s$$

wherein $R_{10}$ is an organic residue of an organic compound having at least one active hydrogen, s is an integer of at least 1 up to the number of active hydrogens contained by the organic compound, $R_{11}$ and $R_{12}$ may be the same or different and can be hydrogen and alkyl (including hydroxy- and halo-substituted alkyl) of, for example, 1 to 28 carbons, and r is an integer of at least 1, say, 1 to about 50.

Organic compounds having active hydrogens include alcohols (mono-, di- and polyhydric alcohols), phenols, carboxylic acids (mono-, di- and polyacids), and amines (primary and secondary). Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms.

Particularly preferred alcohols are primary and secondary monohydric alcohols which are straight or branched chain such as methanol, ethanol, propanol, Pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenyls of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

The alkylene oxides which provide the oxyalkylene units in the ethoxylated products include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorhydrin and epibromhydrin. The preferred alkylene oxides are ethylene oxide and propylene oxide.

The selection of the organic residue and the oxyalkylene moieties is based on the particular application of the resulting alkoxylation product. Advantageously, narrow distributions can be obtained using a wide variety of compounds having active hydrogens, especially monohydric alcohols, which provide desirable surfactants. Because of the narrow distribution of the alkoxylation product mixture, especially attractive alkoxylation products are surfactants in which certain hydrophilic and lipophilic balances are sought. Hence, the organic compound often comprises a monohydric alcohol of about 8 to 20 carbons and the alkylene oxide comprises ethylene oxide.

While the processes described herein are capable of selectively providing narrow distributions of alkoxylates with the most prevalent having as low as one mole of oxyalkylene per mole of active hydrogen site, a particular advantage exists in the ability to provide a narrow distribution at higher levels of alkoxylation, e.g., wherein the most prevalent specie has at least 4 oxyalkylene units. For some surfactant applications, the most prevalent alkoxylation specie has 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation is narrow, but not so narrow that a range of activity is lost.

Moreover, the relatively symmetrical distribution of alkoxylate species that can be provided by this invention enhances that balance while providing a mixture that exhibits desirable physical properties such as cloud point, freeze point, viscosity, pour point and the like. For many alkoxylation mixtures of this invention, the species falling within the range of $\bar{n}$ plus or minus two comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 20 to about 30 weight percent, e.g., about 22 to 28 weight percent, to enhance the balance of the composition.

Another class of alkoxylation product mixtures are the poly(oxyethylene)glycols. For instance, triethylene glycol and tetraethylene glycol find application in gas dehydration, solvent extraction and in the manufacture of other chemicals and compositions. These glycols can be prepared by the ethoxylation of ethylene glycol and diethylene glycol. Advantageous processes of this invention enable ethoxylate product compositions containing at least about 80, say, about 80 to 95, weight percent of triethylene glycol and tetraethylene glycol.

Among the most commercially important alkoxylation products are those which utilize water or an alcohol (monols, glycols, polyols, etc.) as starter (initiator) and ethylene oxide, propylene oxide, or an ethylene oxide/propylene oxide mixture as the 1,2-alkylene oxide monomer. Such alcohol ethoxylates encompass a myriad of structures, compositions and molecular weights intended for service in a diversity of applications ranging from heavy duty industrial end uses such as solvents and functional fluids to ultra-sophisticated, consumer oriented end uses such as in pharmaceutical, personal care and household goods. The calcium sulfate catalyst used in the instant invention finds utility in the manufacture of a broad range of alkoxylation products, but is particularly useful in the manufacture of alkoxylates designed for service in sophisticated, consumer-oriented end use areas of application where product quality demands are stringent. Among the many types of alkoxylates which are used in such applications, two of the most prominent are the poly(oxyethylene)glycols and the fatty alcohol ethoxylates. The Poly(oxyethylene)glycols, known under such tradenames as CARBOWAX®, POLYGLYCOL E®, PLURACOL E®, etc., are manufactured by ethoxylation of ethylene glycol or one of its homologues; they are produced over a molecular weight range of about 200 to about 8,000. The fatty alcohol ethoxylates, known under such non-ionic surfactant tradenames as NEODOL®, ALFONIC®, TERGITOL®, etc., are manufactured by ethoxylation of linear or branched $C_{10}$–$C_{16}$ saturated alcohols; they are produced over a molecular weight range of about 300 to about 800. It is in the production of these and other performance type, premium quality ethoxylates that the heterogeneous catalysts of the instant invention offer maximum advantages relative to the usual homogeneous ethoxylation catalysts (NaOH, KOH, etc.) which must be precipitated/filtered or ion exchanged and removed ultimately from the finished product.

This invention is further illustrated by the following examples.

EXAMPLE 1

To a stirred reaction flask equipped with a thermometer and nitrogen inlet and outlet was added 5.50 grams of calcium sulfate (2 hydrate), commercially available from Aldrich Chemical Company, Inc., Milwaukee, Wis., and 557.6 grams (2.79 moles) of ALFOL® 1214 alcohol (a mixture of C-12 and C-14 linear, primary alcohols), commercially avavailable from Vista Chemical Company, Houston, Tex. The resulting mixture stirred at a temperature of 45° C. for a period of 3 hours under an atmosphere of nitrogen. Some 557.0 grams of the mixture was charged to a 2-gallon autoclave which had been previously washed, thoroughly dried, and purged with nitrogen. The autoclave and contents were heated with stirring to a temperature of 160° C., at which temperature the autoclave pressure was adjusted to 20 psig. Ethylene oxide was added manually to the mixture in the autoclave at a temperature of 160° C., until the total pressure reached 60 psig. From that time onward, ethylene oxide was added automatically under control by pressure differential at 60 psig. A description of the automatic addition is as follows:

After a period of time at a temperature of 160° C., some of the ethylene oxide added initially to the autoclave was consumed by reaction and the total pressure fell to below 60 psig. This temporary decrease of pressure automatically triggered the opening of an ethylene oxide addition valve, through which liquid ethylene oxide was added to the autoclave until the pressure of 60 psig had been restored. Upon restoration of pressure, the ethylene oxide addition valve was closed automatically and remained closed until such time as ethylene oxide consumption by reaction again caused the total pressure to fall below 60 psig. At that time, ethylene oxide was again added to the autoclave (addition valve opened) until the 60 psig was restored (addition valve closed). This process was repeated until 708 grams of ethylene oxide had been added (reacted) to the autoclave. Once the 708 grams of ethylene oxide had been added, the automatic addition valve was closed-off and all unreacted (residual) ethylene oxide still present in the autoclave was reacted (cooked-out) by maintenance of the temperature at 160° C. for several hours. Thereafter, the crude product was cooled to a temperature of 65° C. and acidified by addition of 0.65 grams of glacial acetic acid. The acidified mixture was stirred at a temperature of 65° C. for a period of 3 hours, after which it was dumped to a 1-gallon bottle under nitrogen blanket.

Analysis of the product revealed a molecular weight of 431 and a diol content of 6%. Analysis by gas chromatography (weight %) was as follows:

| Adduct | Wt. % |
| --- | --- |
| $E_0$ | 2.4 |
| $E_1$ | 1.7 |
| $E_2$ | 3.3 |
| $E_3$ | 7.7 |
| $E_4$ | 15.1 |
| $E_5$ | 21.9 |
| $E_6$ | 22.0 |
| $E_7$ | 15.4 |
| $E_8$ | 7.7 |
| $E_9$ | 2.1 |
| $E_{10}$ | 0.7 |

The sixth adduct is the most populous one. The sixth adduct plus the fourth, fifth, seventh, and eighth adducts (±2 adducts on either side of the most populous one) equals to 82.1 wt. % of the total population of adducts in the surfactant product.

EXAMPLE 2

To a stirred reaction flask equipped with a thermometer and nitrogen inlet and outlet was added 5.30 grams of calcium sulfate (gamma form), which was vacuum dried, and 530 grams (2.65 moles) of ALFOL® 1214 alcohol (a mixture of C-12 and C-14 linear, primary alcohols), commercially available from Vista Chemical Company, Houston, Tex. The resulting mixture stirred at a temperature of 45° C. for a period of 30 minutes under an atmosphere of nitrogen. Some 530 grams of the mixture was charged to a 2-gallon autoclave which had been previously washed, thoroughly dried, and purged with nitrogen. The autoclave and contents were heated with stirring to a temperature of 160° C., at which temperature the autoclave pressure was adjusted to 20 psig. Ethylene oxide was added manually to the mixture in the autoclave at a temperature of 160° C., until the total pressure reached 60 psig. From that time onward, ethylene oxide was added automatically under control by pressure differential at 60 psig. A description of the automatic addition is as follows:

After a period of time at a temperature of 160° C., some of the ethylene oxide added initially to the autoclave was consumed by reaction and the total pressure fell to below 60 psig. This temporary decrease of pressure automatically triggered the opening of an ethylene oxide addition valve, through which liquid ethylene oxide was added to the autoclave until the pressure of 60 psig had been restored. Upon restoration of pressure, the ethylene oxide addition valve was closed automatically and remained closed until such time as ethylene oxide consumption by reaction again caused the total pressure to fall below 60 psig. At that time, ethylene oxide was again added to the autoclave (addition valve opened) until the 60 psig was restored (addition valve closed). This process was repeated until 702 grams of ethylene oxide had been added (reacted) to the autoclave. Once the 702 grams of ethylene oxide had been added, the automatic addition valve was closed off and all unreacted (residual) ethylene oxide still present in the autoclave was reacted (cooked-out) by maintenance of the temperature at 160° C. for several hours. Thereafter, the crude product was cooled to a temperature of 65° C. and acidified by addition of 0.65 grams of glacial acetic acid. The acidified mixture as stirred at a temperature of 65° C. for a period of 3 hours, after which it was dumped to a 1-gallon bottle under nitrogen blanket.

Analysis of the product revealed a molecular weight of 460 and a diol content of 3%. Analysis by gas chromatography (weight %) was as follows:

| Adduct | Wt. % |
|---|---|
| $E_0$ | 1.6 |
| $E_1$ | 0.9 |
| $E_2$ | 1.8 |
| $E_3$ | 4.4 |
| $E_4$ | 10.2 |
| $E_5$ | 19.0 |
| $E_6$ | 24.4 |
| $E_7$ | 20.9 |
| $E_8$ | 11.7 |
| $E_9$ | 4.2 |
| $E_{10}$ | 0.9 |

The sixth adduct is the most populous one. The combined total of the sixth adduct plus the fourth, fifth, seventh, and eighth equals to 86.2 wt. % of the total population of adducts in the surfactant product.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

I claim:

1. A process for preparing an alkoxylation product mixture having a narrow distribution of alkoxylate species comprising contacting an organic compound having at least one active hydrogen with an alkylene oxide in which the mole ratio of reacted alkylene oxide per active hydrogen is at least about 4 in the presence of a catalytically effective amount of a catalyst consisting essentially of calcium sulfate under alkoxylation conditions sufficient to provide a product mixture characterized by having at least one alkoxylate specie which constitutes about 20 to 40 weight percent of the product mixture; the weight percent of the product mixture having three or more oxyalkylene units than the average peak alkoxylate specie is less than about 12 weight percent of the mixture; the alkoxylate specie having one oxyalkylene group more than that of the most prevalent specie and the alkoxylate specie having one oxyalkylene group less than that of the most prevalent specie are present in a weight ratio to the most prevalent specie of about 0.6:1 to 1:1.

2. The process of claim 1 wherein the organic compound having at least one active hydrogen is an alcohol comprising a monohydric, aliphatic alcohol having from 1 to 7 carbons.

3. The process of claim 2 wherein the monohydric, aliphatic alcohol is selected from methanol, 2-methoxyethanol and 2-(2-methoxyethoxy)-ethanol.

4. The process of claim 1 wherein the organic compound having at least one active hydrogen is an alcohol comprising a dihydric alcohol.

5. The process of claim 4 wherein the dihydric alcohol is ethylene glycol.

6. The process of claim 1 wherein the organic compound having at least one active hydrogen is an alcohol comprising a polyhydric alcohol.

7. The process of claim 6 wherein the polyhydric alcohol is glycerine.

8. The process of claim 1 wherein the alkylene oxide is ethylene oxide.

9. The process of claim 1 wherein the alkylene oxide is ethylene oxide and propylene oxide.

10. The process of claim 1 wherein the organic compound having at least one active hydrogen is an alcohol comprising ethylene glycol.

11. The process of claim 1 wherein the organic compound having at least one active hydrogen is an alcohol comprising a monohydric, aliphatic alcohol having from 8 to 20 carbons.

12. The process of claim 11 wherein the monohydric, aliphatic alcohol is selected from n-dodecanol, a mixture of $C_8$–$C_{10}$ alcohols and a mixture of $C_{12}$–$C_{14}$ alcohols.

13. A process for preparing a nonionic surfactant product mixture comprising alkoxylated derivatives of an alcohol having a narrow distribution of alkoxylate species comprising:
(a) introducing an alkoxylation catalyst consisting essentially of calcium sulfate with a surfactant molecular weight alcohol;
(b) introducing an alkylene oxide under conditions at which an alkoxylation reaction will occur, thereby producing said alkoxylated derivatives of an alcohol in which the mole ratio of reacted alkylene oxide per active hydrogen is at least about 4; and
(c) recovering said alkoxylated derivatives; said nonionic surfactant product mixture characterized by having at least one alkoxylate specie which constitutes about 20 to 40 weight percent of the product mixture; the weight percent of the product mixture having three or more oxyalkylene units than the average peak alkoxylate specie is less than about 12 weight percent of the mixture; the alkoxylate specie having one oxyalkylene group more than that of the most prevalent specie and the alkoxylate specie having one oxyalkylene group less than that of the most prevalent specie are present in a weight ratio to the most prevalent specie of about 0.6:1 to 1:1.

14. The process of claim 13 wherein the alcohol is n-dodecanol or a mixture of $C_{12}$–$C_{14}$ alcohols.

15. The process of claim 13 wherein the alkylene oxide is ethylene oxide.

16. The process of claim 13 wherein the alcohol is a mixture of $C_8$–$C_{10}$ alcohols.

17. The process of claim 13 wherein the alkylene oxide is ethylene oxide and propylene oxide.

18. A process for preparing a poly(oxyalkylene)-glycol product mixture comprising alkoxylated derivatives of an alkylene glycol having a narrow distribution of alkoxylate species comprising:
   (a) introducing an alkoxylation catalyst consisting essentially of calcium sulfate with an alkylene glycol;
   (b) introducing an alkylene oxide under conditions at which an alkoxylation reaction will occur, thereby producing said alkoxylated derivatives of an alkylene glycol in which the mole ratio of reacted alkylene oxide per active hydrogen is at least about 4; and
   (c) recovering said alkoxylated derivatives;
said poly(oxyalkylene)glycol product mixture characterized by having at least one alkoxylate specie which constitutes about 20 to 40 weight percent of the product mixture; the weight percent of the product mixture having three or more oxyalkylene units than the average peak alkoxylate specie is less than about 12 weight percent of the mixture; the alkoxylate specie having one oxyalkylene group more than that of the most prevalent specie and the alkoxylate specie having one oxyalkylene group less than that of the most prevalent specie are present in a weight ratio to the most prevalent specie of about 0.6:1 to 1:1.

19. The process of claim 18 wherein the alkylene glycol is ethylene glycol.

20. The process of claim 18 wherein the alkylene oxide is ethylene oxide.

21. The process of claim 18 wherein the alkylene oxide is ethylene oxide and propylene oxide.

22. A method for the alkoxylation of an alcohol comprising alkoxylating the alcohol with an alkylene oxide in which the mole ratio of reacted alkylene oxide per active hydrogen is at least about 4 in the presence of a catalyst consisting essentially of calcium sulfate to produce a product mixture comprising alkoxylates of the alcohol under alkoxylation conditions, said product mixture characterized by having at least one alkoxylate specie which constitutes about 20 to 40 weight percent of the product mixture; the weight percent of the product mixture having three or more oxyalkylene units than the average peak alkoxylate specie is less than about 12 weight percent of the mixture; the alkoxylate specie having one oxyalkylene group more than that of the most prevalent specie and the alkoxylate specie having one oxyalkylene group less than that of the most prevalent specie are present in a weight ratio to the most prevalent specie of about 0.6:1 to 1:1.

23. The process of claim 22 in which the alkoxylate species falling within the range of the weight average alkoxylation number plus or minus two comprise between about 80 and 95 weight percent of the product mixture.

24. The process of claim 22 in which the most prevalent alkoxylate specie has 6, 7, 8, 9, 10, 11 or 12 oxyalkylene units.

25. The process of claim 1 wherein the alkoxylation product mixture has an alkoxylation specie distribution corresponding to the formula $$P_n = A \times e^{-(n-\bar{n})^2/(2.6+0.4\bar{n})}$$

wherein n is an integer of at least one and is the number of oxyalkylene groups per reactive hydrogen site of the alcohol for the alkoxylate specie, $\bar{n}$ is the weight average oxyalkylene number of the mixture, A is the weight percent of the most prevalent alkoxylate specie in the mixture and $P_n$ is, within plus or minus two percentage points, the weight percent of the alkoxylate specie having n oxyalkylene groups per active hydrogen site, based on the weight of the mixture.

26. The process of claim 25 in which the most prevalent alkoxylate specie has 6, 7, 8, 9, 10, 11 or 12 oxyalkylene units.

* * * * *